US011622739B2

(12) United States Patent
Parthasarathy et al.

(10) Patent No.: US 11,622,739 B2
(45) Date of Patent: Apr. 11, 2023

(54) INTRA-SURGERY IMAGING SYSTEM

(71) Applicant: General Electric Company, Schenectady, NY (US)

(72) Inventors: Gautam Parthasarathy, Niskayuna, NY (US); Bruno Kristiaan Bernard De Man, Clifton Park, NY (US); Ronald Andrew von Jako, Melrose, MA (US); Ross Christopher Stalter, Hartland, WI (US)

(73) Assignee: General Electric Company, Schenectady, NY (US)

( * ) Notice: Subject to any disclaimer, the term of this patent is extended or adjusted under 35 U.S.C. 154(b) by 65 days.

(21) Appl. No.: 16/725,532

(22) Filed: Dec. 23, 2019

(65) Prior Publication Data

US 2021/0186442 A1 Jun. 24, 2021

(51) Int. Cl.
*A61B 6/00* (2006.01)
(52) U.S. Cl.
CPC .......... *A61B 6/4441* (2013.01); *A61B 6/4007* (2013.01)
(58) Field of Classification Search
CPC ............................ A61B 6/4441; A61B 6/4007
See application file for complete search history.

(56) References Cited

U.S. PATENT DOCUMENTS

| 4,129,783 | A | * | 12/1978 | Houston | ................. | A61B 6/032 378/92 |
|---|---|---|---|---|---|---|
| 5,583,909 | A | | 12/1996 | Hanover | | |
| 6,113,264 | A | * | 9/2000 | Watanabe | ............... | A61B 6/466 378/196 |
| 7,065,393 | B2 | | 6/2006 | Sati et al. | | |
| 7,604,404 | B2 | | 10/2009 | Ohishi et al. | | |
| 7,840,253 | B2 | | 11/2010 | Tremblay et al. | | |
| 8,303,181 | B2 | | 11/2012 | Sukovic et al. | | |
| 9,044,190 | B2 | | 6/2015 | Rubner et al. | | |
| 9,055,912 | B2 | * | 6/2015 | Graumann | ............. | A61B 6/035 |
| 9,713,450 | B2 | | 7/2017 | Claus et al. | | |
| 10,092,265 | B2 | | 10/2018 | Lavallee et al. | | |

(Continued)

FOREIGN PATENT DOCUMENTS

WO WO-0187136 A2 * 11/2001 ............. A61B 34/20

OTHER PUBLICATIONS

Ritterr, Dieter, et al.; "3D Soft Tissue Imaging With a Mobile C-Arm", Computerized Medical Imaging and Graphics, vol. 31, Issue: 2, pp. 91-102, Mar. 2007.

(Continued)

*Primary Examiner* — Christine S. Kim

(57) ABSTRACT

Various embodiments discussed herein utilize a C-shaped imager to provide images with a minimal footprint, such as may be suitable in a surgical context. In addition the systems and methods described herein allow for suitable angular (i.e., azimuthal) scan coverage about the patient. To provide real-time 3D imaging, multiple X-ray tubes or a distributed X-ray source may be employed, coupled with an extended detector or multiple detectors. To reconstruct high-quality volumes, in some implementations reconstruction techniques may be employed that utilize pre-operative (pre-op) computed tomography (CT), magnetic resonance imaging (MRI), ultrasound (U/S), or other suitable modality images or data as prior information.

19 Claims, 9 Drawing Sheets

(56) References Cited

U.S. PATENT DOCUMENTS

| | | | |
|---|---|---|---|
| 2005/0251010 A1* | 11/2005 | Mistretta | A61B 6/507 600/407 |
| 2008/0094396 A1 | 4/2008 | Sabczynsdi et al. | |
| 2011/0075804 A1* | 3/2011 | Boese | H01J 35/065 378/62 |
| 2011/0075809 A1* | 3/2011 | Boese | A61B 6/4014 378/92 |
| 2011/0211666 A1* | 9/2011 | Ying | A61B 6/032 378/9 |
| 2017/0258426 A1* | 9/2017 | Risher-Kelly | A61B 6/12 |
| 2018/0182132 A1* | 6/2018 | Kowarschik | A61B 6/504 |
| 2019/0038245 A1 | 2/2019 | Bailey et al. | |

OTHER PUBLICATIONS

Schnetzke, Marc et al.; "Intraoperative 3D Imaging in the Treatment of Elbow Fractures—A Retrospective Analysis of Indications, Inliaoperative Revision Rates, and Implications in 36 Cases", BMC Medical Imaging, vol. 16, Issue: 1, Dec. 2016.

* cited by examiner

INTRA-SURGERY IMAGING SYSTEM

BACKGROUND

The subject matter disclosed herein relates to imaging techniques suitable for use in a surgical or other interventional and diagnostic context, such as to provide accurate imaging and guidance during a procedure to facilitate performing the procedure.

Various medical procedures are invasive in nature. In practice, these procedures may benefit from the acquisition of image data suitable for discerning and displaying various structures within the patient body and to also facilitate less invasive procedures. For example, such image data may be used to evaluate shape and location of vessels feeding a tumor, safely guide a device or agent to the target while avoiding critical structures (e.g., circumventing specific vessels, nerve roots, organs, or spinal canal) and to orient and guide various instruments and implants, or otherwise navigate a patient's anatomy to accomplish a given treatment or therapy.

By way of example, various surgical applications may benefit from intra-operative imaging to guide the surgery. In particular, such surgical applications may benefit from real-time, high-quality three-dimensional (3D) imaging that can provide real-time feedback and visual guidance in the transverse view to the surgeon. A specific example of one such surgical procedure is spinal fusion, where screws need to be drilled into a complex geometric structure such as the vertebra with high precision and accuracy. In such a context, 2D images do not always provide the necessary precision to accurately estimate the relative position and orientation of screws relative to the key structures of the vertebra. However, imaging systems capable of providing high-quality 3D imaging in a real-time context are typically bulky and obtrusive and then more so when coupled with stereotactic computer-assisted navigation platforms for near-real-time guidance, taking up space near the patient needed by the personnel performing the procedure while maintaining a sterile environment for the patient.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, an X-ray imaging system is provided. In accordance with this embodiment, the X-ray imaging system comprises: a support structure comprising a first arm comprising an array of X-ray emission points and a second arm comprising a detector array. The first arm and the second arm are movable between an open configuration and a closed configuration. The X-ray imaging system of this embodiment further comprises: a system controller in communication with the array of X-ray emission points and the detector array; and a display device configured to display images generated using data acquired using the detector array.

In a further embodiment, a method for imaging a patient is provided. In accordance with this method, a C-shaped imager is positioned proximate to a patient. The C-shaped imager comprises a first arm and a second arm in an open configuration such that the first arm and the second arm go about the patient in the open configuration. The first arm comprises an array of X-ray emission points and the second arm comprises a detector array. The first arm and the second arm are caused to move to a closed configuration about the patient. The closed configuration is suitable for imaging the patient. The C-shaped imager is operated to acquire X-ray projection data over an angular range about the patient. One or more images are generated using the acquired X-ray projection data. The one or more images are displayed in real-time.

In one embodiment, an X-ray imaging system is provided. In accordance with this embodiment, the X-ray imaging system comprises: a C-shaped imager comprising: a first arm comprising an array of multiple X-ray emission points and a second arm comprising a detector configured to detect X-rays emitted by the array of multiple X-ray emission points. The array of multiple X-ray emission points and the detector provide at least 90 degrees of angular coverage with respect to an imaged volume when the first arm and the second arm are in the closed configuration. The X-ray imaging system of this embodiment further comprises: a system controller in communication with the array of X-ray emission points and the detector and a display device configured to display images generated using data acquired using the detector.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
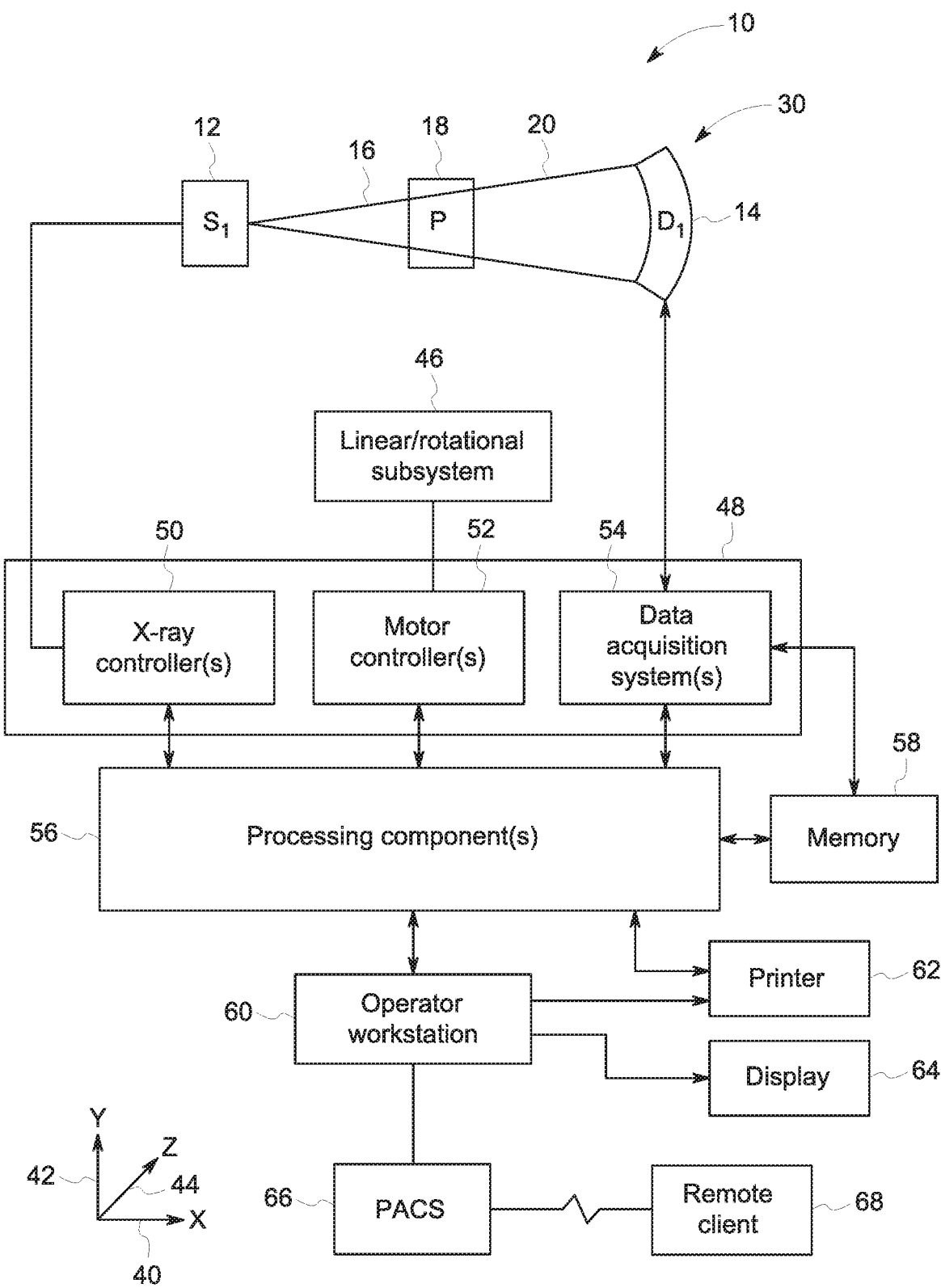
FIG. 1 is a diagrammatical view of an imaging system for use in producing images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Conventional C-arm fluoroscopy is commonly used by surgeons and interventionalists but has limitations with a need to reposition the fluoroscope repeatedly to obtain adequate two-dimensional anatomical target viewing for image guidance techniques. Such two-dimensional (2D) imaging in complex anatomical targets is limiting when additional visual information to the operator is often desired.

Various available technologies have been applied to solve the problem limitations and challenges associated with having only two-dimensional operative guidance. The use of pre-operative multimodal images (e.g. CT/MR) coupled together with optical or electromagnetic (EM) based stereotactic computer navigation systems that register pre-operative acquired (CT/MR) images to the patient onto a monitor, have been developed to enhance image guidance. The disadvantage of these technologies are that the historic (i.e., pre-operative or pre-op) images do not provide necessary real-time intraoperative updates. As surgery progresses, bone and tissue are manipulated, altered, or removed and anatomical landmarks are often displaced from their preoperative position, which repeatedly challenges surgical precision. In addition, these technologies are associated with some additional operative set-up time for the process of registration between the pre-op images and the patient intraoperatively with random optical infrared line of sight or field distortion issues associated with magnetic interference in EM technology while navigating the anatomical images. In response, other technologies have also been developed with near real-time options to provide intraoperative virtual tomographic scans of the spine or extremities. Such techniques are typically based on rotating an isocentric C-arm up to a 190-degree arc around the operating table and patient at the time of surgery. A series of "captured" fluoroscopic images are then reconstructed into 3D-like; axial, sagittal, and coronal views which may be referred to as a virtual CT scan. The limitations of these devices include image quality challenges in various patients and the associated interruption of the surgical procedure to allow time and space for this imaging procedure. Newer technology has also been developed utilizing flat panel detectors within a "ring" shaped mobile device, but these have a relatively large footprint and therefore cannot effectively be performed in real-time without interrupting the surgical procedure. In general, the limitations of all these technologies in addition to image quality, ease of use and size, is the absence of consecutive real-time clinical-quality CT image updates that obviate the need for a time-consuming gantry rotation, data acquisition, and image reconstruction delay that render routine use as impractical.

As discussed herein, various implementations of the present invention may utilize a C-shaped imager system to provide images with a minimal footprint around the patient so as to be unobtrusive. In such an embodiment, the medical personnel are provided good access to the patient, in contrast to other types of imaging modalities capable of providing comparable image data. In addition, the systems and methods described herein allow for greater angular (i.e., azimuthal) scan coverage about the patient using one or both of mechanical (i.e., structural) features or electrical features. To provide real-time 3D imaging, multiple X-ray tubes or a distributed X-ray source may be employed, coupled with an extended detector or multiple detectors. To reconstruct high-quality volumes, in some implementations reconstruction techniques may be employed that utilize pre-operative (pre-op) computed tomography (CT), magnetic resonance imaging (MM), ultrasound (U/S), or other suitable modality images or data as prior information. By providing a real-time imaging solution suitable for use in a surgical or interventional environment, situations may be avoided or minimized where a patient is returned to surgery for additional procedures due to post-surgical imaging detecting the need for additional revision.

Examples of implementations as described herein allow data to be acquired over a greater angular range than is typically associated with tomosynthesis techniques (which are associated with three-dimensional (3D) image reconstructions but offering relatively poor spatial resolution in the third dimension and are therefore sometime referred to as 2.1D). In certain embodiments, the present techniques allow acquisition of image data over a sufficient angular range to generate three-dimensional (3D) images having isotropic voxels (i.e., voxels that can be viewed or projected from any angle with the same resolution from all views, as opposed to a limited number of view directions associated with tomosynthesis) or oblique formats thereof. Further, the systems described herein have a reduced footprint relative to other systems capable of generating 3D images, such that the systems can be positioned or operated at the bedside of a patient undergoing a surgical or other interventional procedure, such as to provide real-time 3D intra-operative imaging and image-guidance. Such real-time 3D images may be useful in supporting and simplifying surgical procedures. Additionally, the imaging techniques disclosed herein, which may provide true-3D images having isotropic voxels (or oblique reformats thereof) and image quality comparable to standard, whole-body CT systems, may enable additional intraoperative imaging that is currently not available for visualizing soft tissue structures in real-time.

With the preceding in mind, an example of a dual-arm (e.g., C-shaped imager) imaging system 10 suitable for acquiring X-ray attenuation data for reconstruction as discussed herein is provided in FIG. 1. Relative to other imaging modalities (e.g., computed tomography (CT)), the dual-arm imaging system 10 of the present invention has a reduced footprint, providing the opportunity to perform image acquisition in circumstances where other imaging approaches are prohibited due to space considerations in a procedure room.

In the embodiment illustrated in FIG. 1, imaging system 10 includes a source of X-ray radiation 12 and a detector 14. The X-ray source 12 may be an X-ray tube or any other source of X-ray radiation suitable for the acquisition of medical or other images. The X-rays 16 generated by the source 12 pass into a region in which a patient 18, is positioned during a procedure. In the depicted example, the X-rays 16 are collimated to be a fan-shaped (planar) or cone-shaped (volumetric) beam, e.g., a fan-beam or cone-beam, which passes through the imaged volume. In a context where the imaging system 10 is used in a surgical support or navigation role, a collimator may be used to constrain the X-rays 16 to only irradiate a field-of-view (FOV) corresponding to specific portions of the patient 18, such as a region-of-interest (ROI) and to avoid other portions of the patient (such as sensitive organs) or the medical personnel. By way of example, in certain scenario specific implementations, different FOVs may be appropriate, such as a 9 inch and a 12 inch FOV, with the 9 inch FOV suitable for spine imaging and the 12 inch FOV suitable for peripheral (e.g., outside heart) endovascular imaging.

A portion of the X-ray radiation 20 passes through or around the patient 18 (or other subject of interest) and impacts a detector array, represented generally as the detector 14. Detector elements of the detector 14 produce electrical signals that represent the intensity of the incident X-rays 20. These signals are acquired and processed, as discussed herein, to reconstruct images of the features within the patient 18.

In the present example, the source 12 and detector 14 may be a part of an imager subsystem 30. In accordance with present embodiments, the source 12 and detector 14 of the imager 30 may be moved relative to the patient or imaged object along one or more axes during a scan procedure during which projection data is acquired. For example, the imager 30 may move about a first axis of rotation 40, a second axis of rotation 42, or a third axis of rotation 44, or any combination thereof. In one embodiment, the translation and rotation of the imager 30 may be determined or coordinated in accordance with a specified protocol.

The movement of the imager 30 may be initiated and/or controlled by one or more linear/rotational subsystems 46. The linear/rotational subsystems 46 may include support structures, motors, gears, bearings, and the like, that enable the rotational and/or translational movement of the imager 30. In one embodiment, the linear/rotational subsystems 46 may include a structural apparatus (e.g., a C-shaped imager apparatus having rotational movement about at least two axes) supporting the source 12 and the detector 14.

A system controller 48 may govern the linear/rotational subsystems 46 that initiate and/or control the movement of the components of the imager 30. In practice, the system controller 48 may incorporate one or more processing devices that include or communicate with tangible, non-transitory, machine readable media collectively storing instructions executable by the one or more processors to perform the operations described herein. The system controller 48 may also include features that control the timing of the activation of the source 12, for example, to control the acquisition of X-ray attenuation data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imager. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the imager 30 and the linear/rotational subsystems 46. In the illustrated embodiment, the circuitry may include an X-ray controller 50 configured to operate the X-ray source 12. Circuitry of the system controller 48 may also include one or more motor controllers 52. The motor controllers 52 may control the activation of various components that are responsible for moving the source 12 and the detector 14. In other words, the motor controllers may implement a particular acquisition trajectory or motion for the components of the imager 30.

The system controller 48 is also illustrated as including one or more data acquisition systems 54. Generally, the detector 14 may be coupled to the system controller 48, and more particularly to the data acquisition systems 54. The data acquisition systems 54 may receive data collected by read out electronics of the detector 14 and in certain embodiments may process the data (e.g., by converting analog to digital signals or to perform other filtering, transformations, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform image acquisition and reconstruction techniques. Further, the processing components 56 and the memory components 58 may coordinate in order to perform various image reconstruction processes.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared throughout the imaging facility and may also be shared with other facilities, for example, a remote client 68. The remote client 68 may include hospitals, doctors' offices, or any other similar client.

Figure 2:
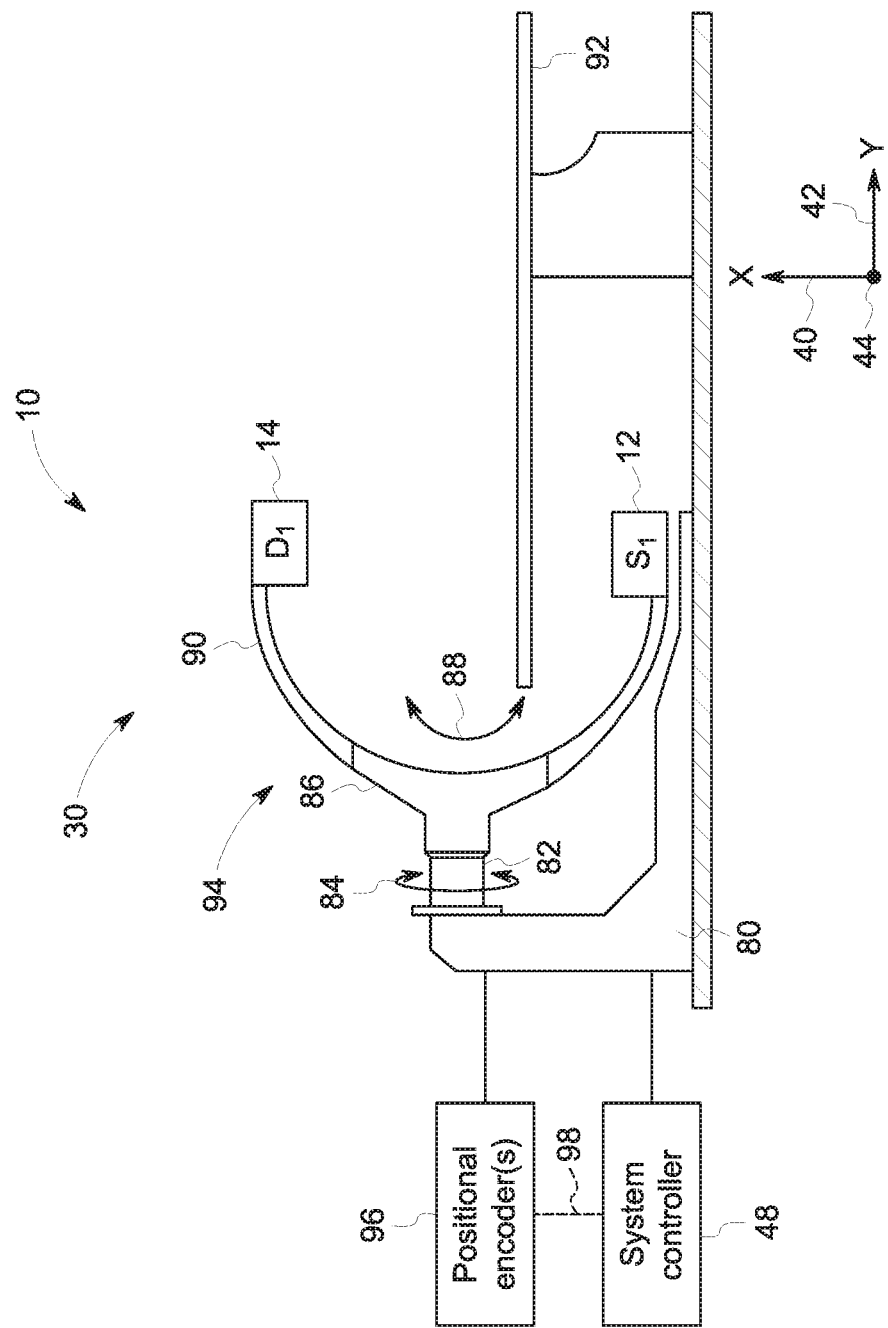
FIG. 2 is a schematic side view of a C-shaped imager representing features of such an imager, in accordance with aspects of the present disclosure.

Various aspects of the present approaches may be further appreciated with respect to FIG. 2, which provides useful context and background in the depiction of a C-shaped imager system, which may have certain features in common with certain implementations of the present invention. In this example, the imager 30, as illustrated, includes a base 80 and a rotatable extension 82 extending from the base 80. In the illustrated embodiment, the base 80 is a floor-mounted base such that the imager 30 may be secured to a floor of an imaging area in which it is positioned. In other embodiments, however, the base 80 may be secured to other surfaces (e.g., a wall or ceiling) and/or may be mobile or movable, such as to be moved toward or away from a patient undergoing a procedure for on-demand imaging during the procedure.

The rotatable extension 82 is depicted as extending generally along the second axis of rotation 42, and enables the source 12 and the detector 14 to move about the second axis of rotation 42. For example, the rotatable extension 82 may enable the source 12 and the detector 14 to move about the second axis of rotation 42 in a manner that maintains their position relative to one another throughout the movement. The rotation enabled by the rotatable extension 82 is shown as double-headed arrow 84. The rotatable extension 82 is coupled to a moving structure 86 (e.g., directly or indirectly via an extension arm), which enables the source 12 and the detector 14 to move about the third axis of rotation 44. This rotation about the third axis of rotation 44 is depicted as double-headed arrow 88.

The moving structure 86 may be a geared or track structure that is motively coupled to a support structure 90 that physically supports the source 12 and the detector 14, and may be in the form of a C-shaped imager, or any other shape (e.g., other dual-arm shapes) that positions the source 12 and the detector 14 on either side of the patient 18. As illustrated, the support structure 90 includes an arcuate structure that extends from a first side of a patient table 92, around the patient table 92, and to a second side of the patient table 92. In this way, the source 12 and the detector 14 generally remain positioned at opposite ends and/or on opposite sides of the patient (not shown) positioned on patient table 92. Together, the base 80, the rotatable extension 82, the moving structure 86, and the support structure 90 may be considered to be the structure 94 of the imager 30.

The imager 30 may include various motors, actuators, or other features responsible for movement of the various structures of the imager 30, and they may be communicatively coupled to one or more positional encoders 96. The one or more positional encoders 96 may encode the respective positions of any one or more components of the imager 30 in a manner that facilitates processing by the system controller 48. In such an implementation, the positional encoders 96 may provide feedback 98 (for example via wired or wireless signals) to the system controller 48. The system controller 48 may use this feedback 98 to control the imager 30.

As an example, the system controller 48 may simultaneously move the source 12 and the detector 14 together about the first axis of rotation 40, the second axis of rotation 42, or the third axis of rotation 44, or any combination thereof, and obtain X-ray attenuation data for a subset of the traversed view angles. In one embodiment, the system controller 48 may receive positional information from the positional encoders 96 relating to the imager 30 and may calculate a trajectory (or update a modeled trajectory) for either or for both of the source and detector 12, 14 using this positional feedback information.

Furthermore, the system controller 48 or other image reconstruction circuitry may synthesize one or more images (e.g., volumetric images) using data obtained by the imager 30. Reconstruction algorithms may be used to reconstruct a 3D volumetric image of the imaged region of interest. To reconstruct high-quality volumes, in some implementations reconstruction techniques may be employed that utilize pre-operative (pre-op) computed tomography (CT), magnetic resonance imaging (MRI), ultrasound (U/S), or other suitable modality images or data as prior information. In one embodiment, the imager 30 may perform an acquisition of data using an acquisition trajectory over which the source 12 and detector 14 move relative to the patient 18.

With the preceding in mind, aspects of the present invention may share certain features with the C-shaped imager system shown in FIG. 2, but may allow for greater angular (i.e., azimuthal) scan coverage about the patient using one or both of mechanical (i.e., structural) features or electrical features. To provide real-time 3D imaging, multiple X-ray tubes or a distributed X-ray source may be employed, coupled with an extended detector or multiple detectors. For example, in certain implementations an array of X-ray sources may be provided to transmit X-rays towards a patient over a wide angular range and an extended detector may be provided to detect the X-rays.

Examples of implementations as described herein allow data to be acquired over a greater angular range (e.g., an angular range greater than 70°, such as 90° or greater) than is typically associated with tomosynthesis techniques (which are typically associated with angular acquisition ranges of approximately 30° to 50° and which are associated with limited spatial resolution in a third dimension). In certain embodiments, the present techniques allow acquisition of image data using a curved array of X-ray emission points (e.g., from two emission points up to a thousand emission points) and a curved detector array over a sufficient angular range to generate three-dimensional (3D) images having isotropic voxels or oblique reformats thereof. Such curved designs as discussed herein may allow imaging over a greater angular range than may be obtained with a flat X-ray source and/or detector array. Further, the systems described herein have a reduced footprint relative to other systems capable of generating 3D images, such that the systems can be positioned or operated at the bedside of a patient undergoing a surgical or other interventional procedure, such as to provide real-time 3D intra-operative imaging and image-guidance. For example, the imager may be mobile (e.g., on wheels), so it can easily be moved to or within the surgical suite. Real-time 3D images acquired using such a system may be useful in supporting and simplifying surgical procedures. Additionally, the imaging techniques disclosed herein, which may provide true-3D images having isotropic voxels (or oblique reformats thereof) and image quality comparable to standard CT systems, may enable additional intraoperative imaging that is currently not available for visualizing soft tissue structures in real-time.

Figure 3A:
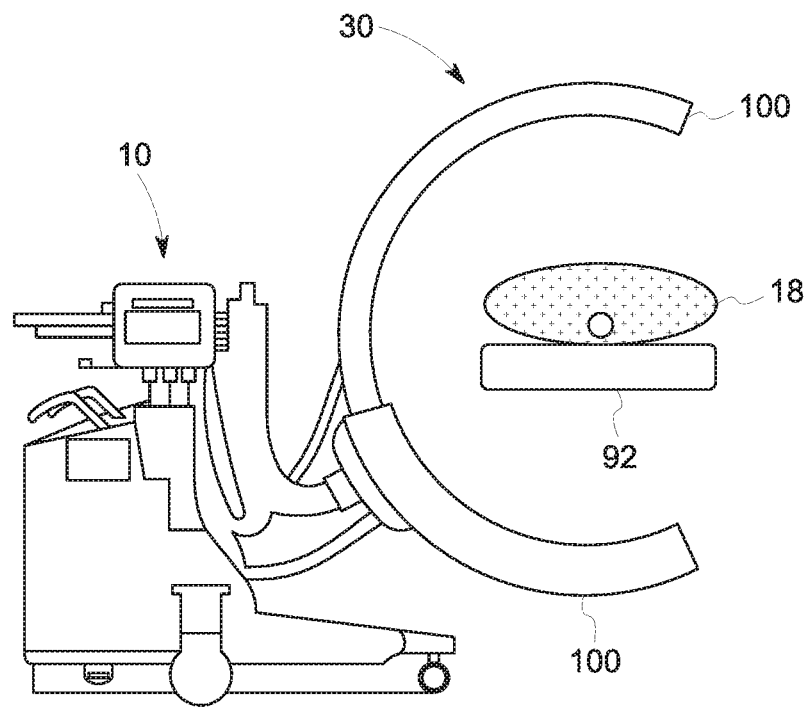
FIG. 3A depicts a first configuration of a C-shaped imager in an open configuration, in accordance with aspects of the present disclosure.
Figure 3B:
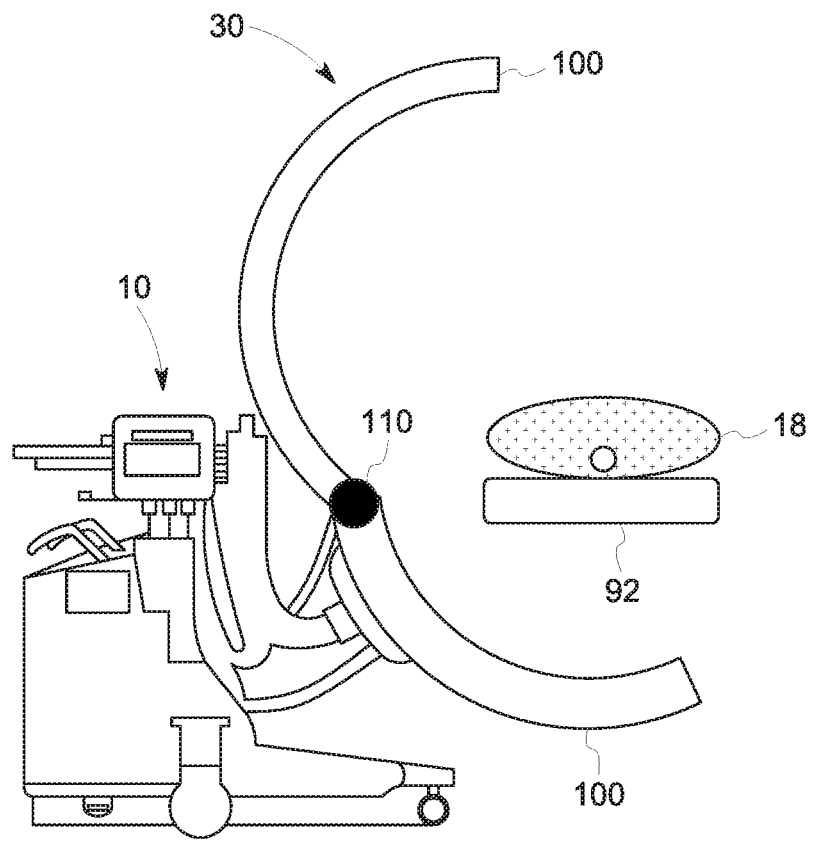
FIG. 3B depicts a second configuration of a C-shaped imager in an alternative open configuration, in accordance with aspects of the present disclosure.
Figure 4:
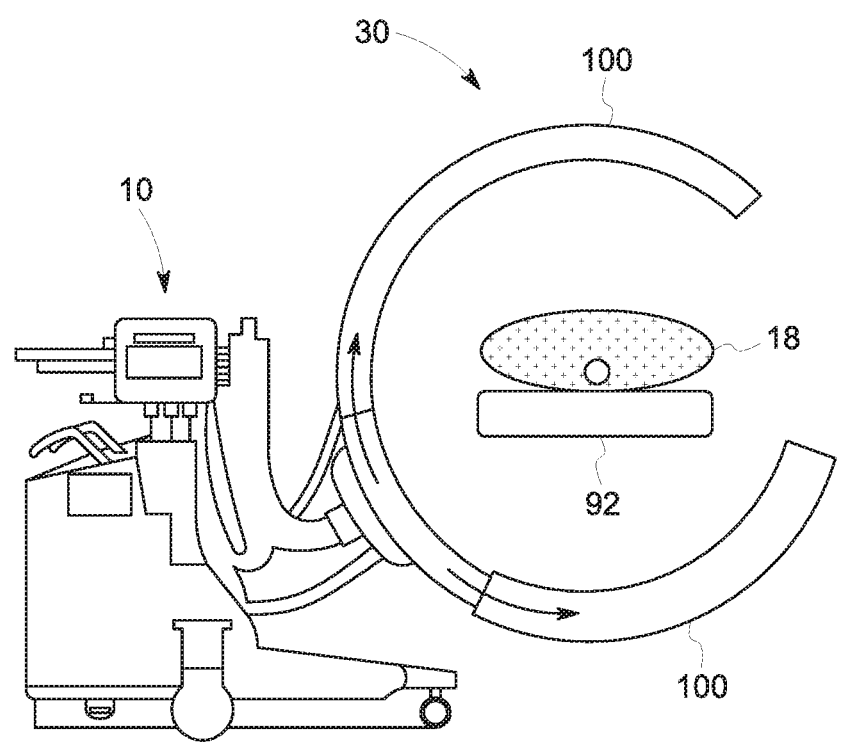
FIG. 4 depicts a C-shaped imager in a closed configuration, in accordance with aspects of the present disclosure.

Turning to FIGS. 3A and 3B, schematic illustrations are provided of a C-shaped imager system in an open position in accordance with aspects of the present disclosure. As used herein, the "C" shape descriptor references that, at least in certain operational configurations or modes, the imager is open on one side so as to be able to slide around a surgery table, patient bed or support, and the patient. In FIG. 3A the C-shaped imager is illustrated in which the arms 100 are in an open configuration suitable for moving or positioning the imager subsystem 30 about a patient 18 placed table 92 or bed. In FIG. 3B, the imager subsystem 30 is shown as being hinged 110 so as to allow the arms 100 of the C-structure to be opened in a configuration suitable for positioning and closed to an operational position. Turning to FIG. 4, a schematic illustration is provided of the C-shaped imager with the arms 100 of the system closed or extended to an operational configuration. Thus, the illustration shown in FIG. 4 may correspond to a state in which the hinged arms 100 of FIG. 3B are swung to a closed position or in which the arms 100 of system of FIG. 3A are extended or slid to an operational position (shown by arrows in FIG. 4) in which a greater angular range of the patient 18 is encompassed. With respect to these examples, as well as the following examples, one arm 100 (e.g., the upper arm 100) may accommodate a curved detector array while the opposing arm (e.g., the lower arm 100) may accommodate a curved array of X-ray emission points (such as one or more discrete emission points per X-ray source or generating device.

Figure 5A:
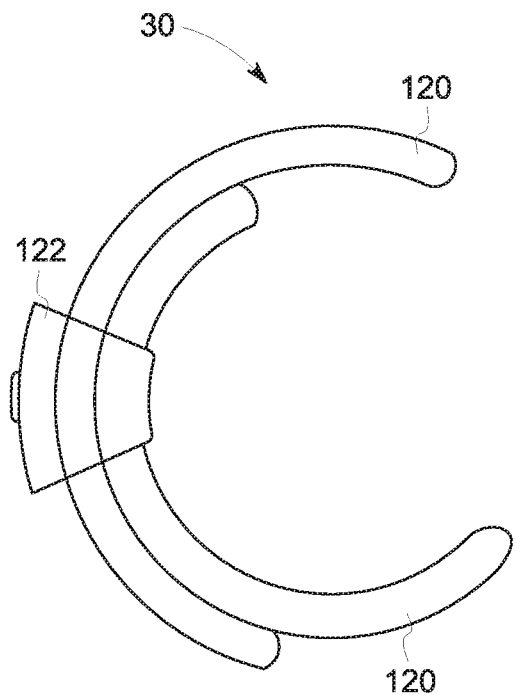
FIG. 5A depicts an implementation of arms of one implementation of a C-shaped imager in an open configuration, in accordance with aspects of the present disclosure.
Figure 5B:
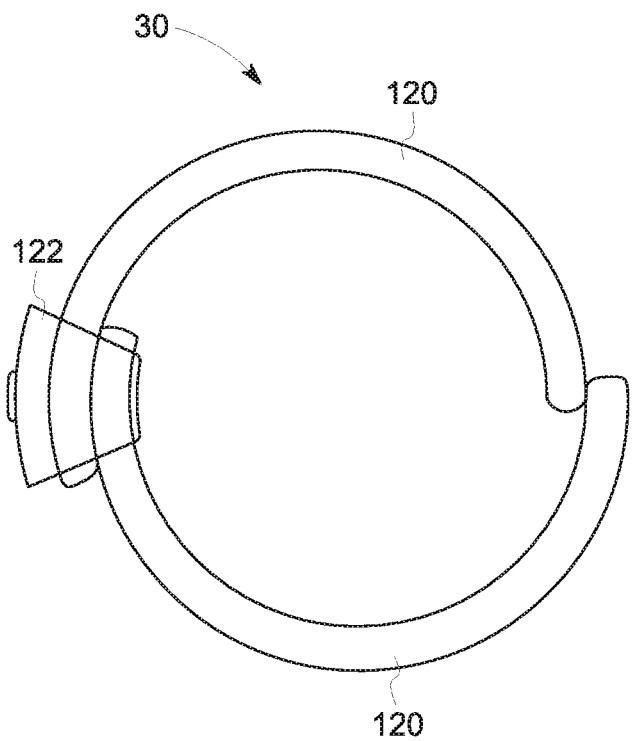
FIG. 5B depicts an implementation of arms of one implementation of a C-shaped imager in a closed configuration, in accordance with aspects of the present disclosure.

Turning to FIGS. 5A and 5B, these figures depict further examples of a C-shaped imager arrangement in which the respective arms slide with respect to one another to transition from an open position to a closed position. In this example, the sliding arrangement is accomplished by using separate, arcuate structures 120 that may slide or be moved with respect to one another at along a motor or guide component 122. As shown in FIGS. 5A and 5B a pair of arcuate structures 120 are provided that are moved by or with respect to the motor or guide component 122 to achieve different degrees of closure of the imager subsystem 30. For example, in FIG. 5A, an open or mostly open configuration is shown in which the imager subsystem 30 can be easily positioned with respect to a patient or patient support. In FIG. 5B, the arcuate structures 120 have been moved relative to the motor or guide component 122 so that the imager subsystem 30 is in a closed configuration suitable for acquiring image data over a wide angular range relative to the patient.

While the preceding schematic figures and examples demonstrate various aspects of closed and open configurations of different implementations of an imager subsystem as described herein, the following figures provide additional examples with respect to the operation and/or geometric arrangement of imaging components of such systems. For example, FIGS. 6, 7, 8, and 9 depict various examples of X-ray generation on one arm 100 of the imager subsystem 30 to detector structures on the opposing arm 100.

Figure 6:
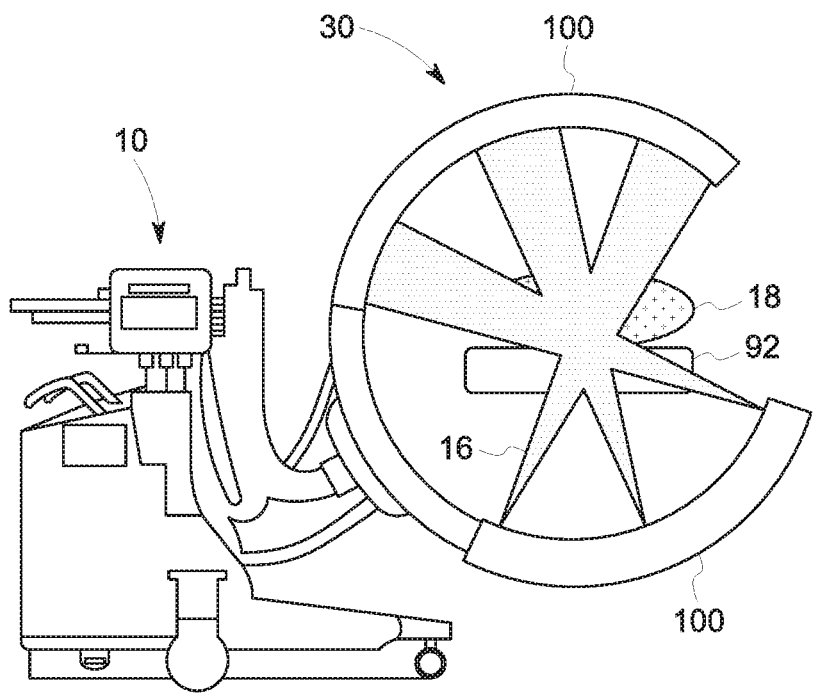
FIG. 6 depicts an implementation of a first simultaneous acquisition implementation of a C-shaped imager system, in accordance with aspects of the present disclosure.
Figure 7:
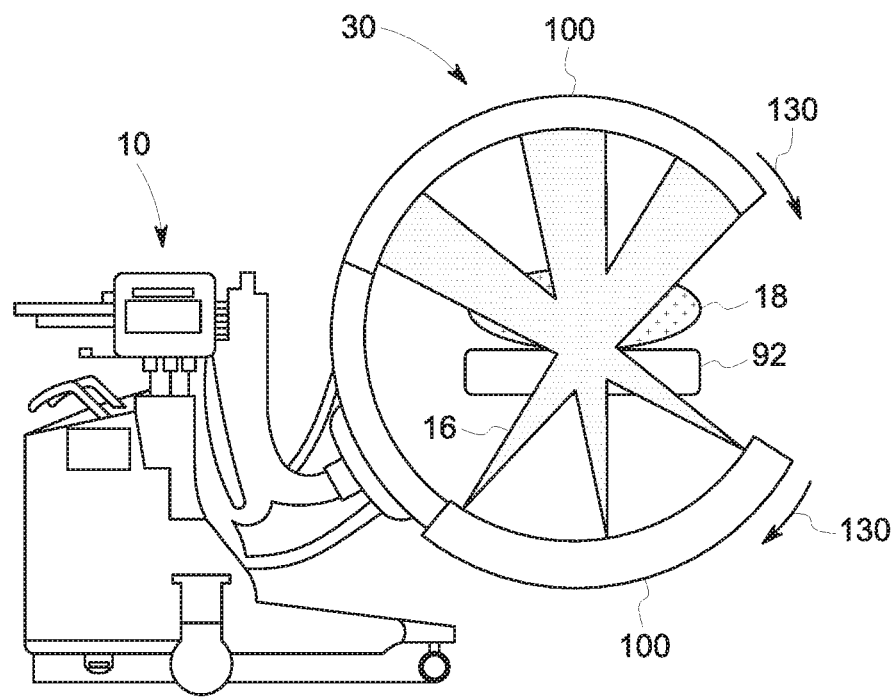
FIG. 7 depicts an implementation of a second simultaneous acquisition implementation of a C-shaped imager system, in accordance with aspects of the present disclosure.

In the examples of FIGS. 6 and 7, simultaneous X-ray emission from multiple X-ray sources on one arm 100 to separate detector regions on the opposite arm 100 of the imager subsystem 30 is depicted. In FIG. 6, an example is depicted in which there are multiple separate and distinct X-ray sources that simultaneously emit X-rays toward separate detector regions on an opposing arm 100 of the imager subsystem 30. In this example, the respective arms 100 of the imager subsystem 30 remain stationary. Conversely, in FIG. 7, the multiple separate and distinct X-ray sources simultaneously emit X-rays toward separate detector regions on the opposing arm 100 of the imager subsystem 30 and the arms 100 also rotate over a limited range (e.g., 90° or less), as shown by directional arrows 130, so as to provide further or more complete angular coverage about the patient 18 compared to the case where only the angular sizes of the source and detector defined the angular coverage.

Figure 8:
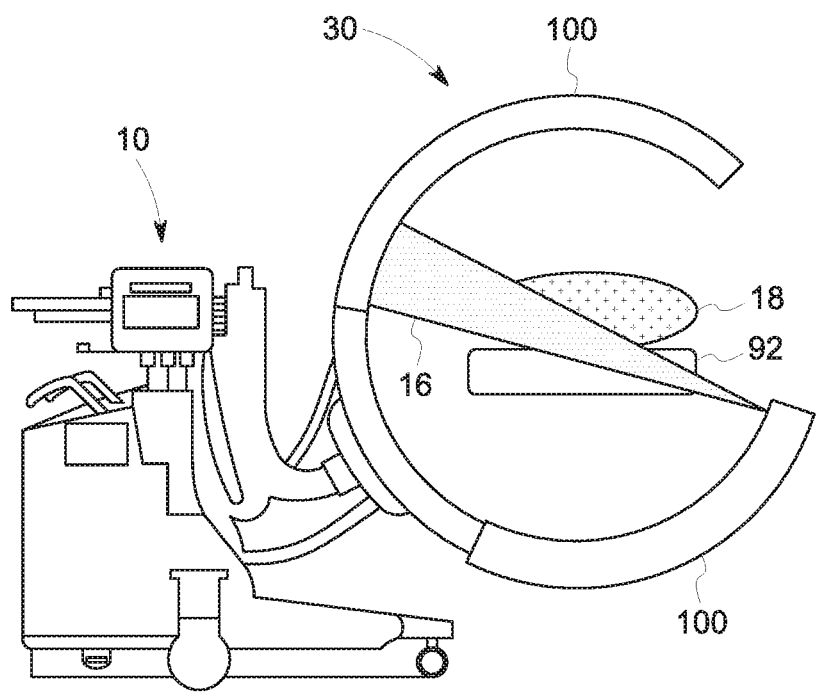
FIG. 8 depicts an implementation of a first sequential acquisition implementation of a C-shaped imager system, in accordance with aspects of the present disclosure.
Figure 9:
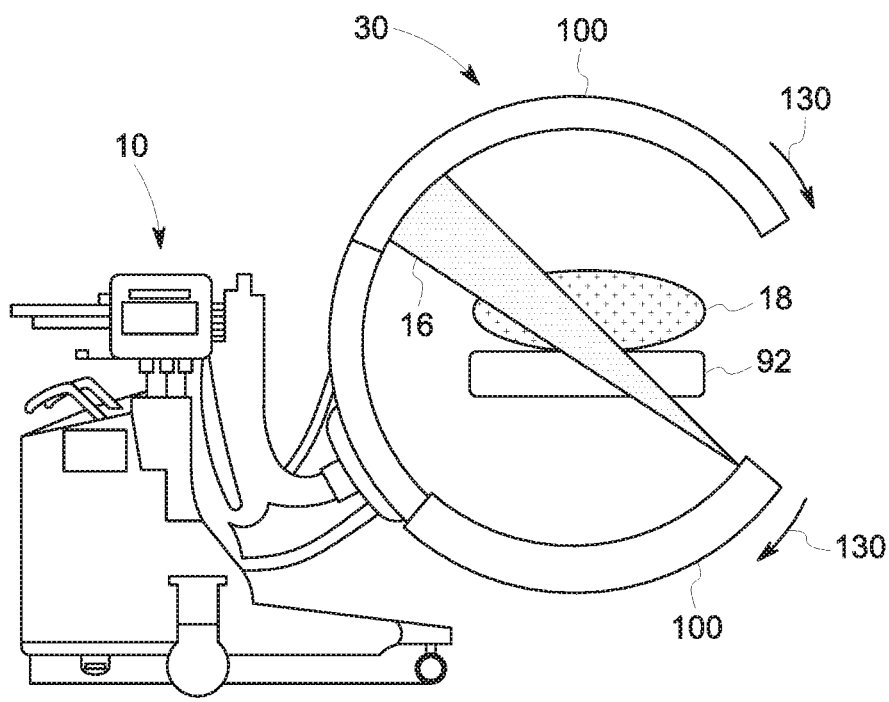
FIG. 9 depicts an implementation of a second sequential acquisition implementation of a C-shaped imager system, in accordance with aspects of the present disclosure.
Figure 10:
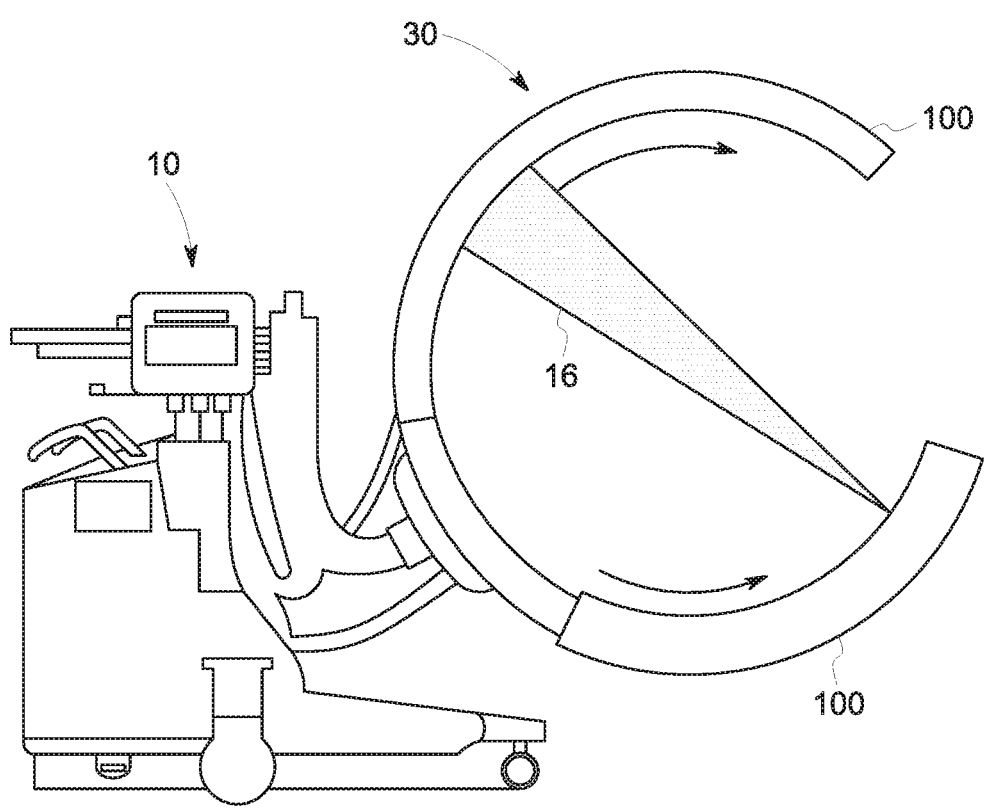
FIG. 10 depicts an implementation of a rotatable acquisition implementation of a C-shaped imager, in accordance with aspects of the present disclosure.

While FIGS. 6 and 7 depict scenarios in which simultaneous X-ray emission from multiple source locations is contemplated, FIGS. 8 and 9 depict other example implementations in which there is sequential X-ray emission from multiple X-ray sources on one arm 100 to respective detector regions on the opposite arm 100 of the imager subsystem 30. In FIG. 8, an example is depicted in which there are multiple separate and distinct X-ray sources that sequentially emit X-rays toward respective detector regions on an opposing arm 100 of the imager subsystem 30 such that only one (or some subset) of emission locations are active at a given time. In this example, the respective arms 100 of the imager subsystem 30 remain stationary. Conversely, in FIG. 9, the multiple separate and distinct X-ray sources sequentially emit X-rays toward respective detector regions on the opposing arm 100 of the imager subsystem 30 and the arms 100 also rotate (as shown by directional arrows 130) so as to provide further or more complete angular coverage about the patient 18.

Figure 11:
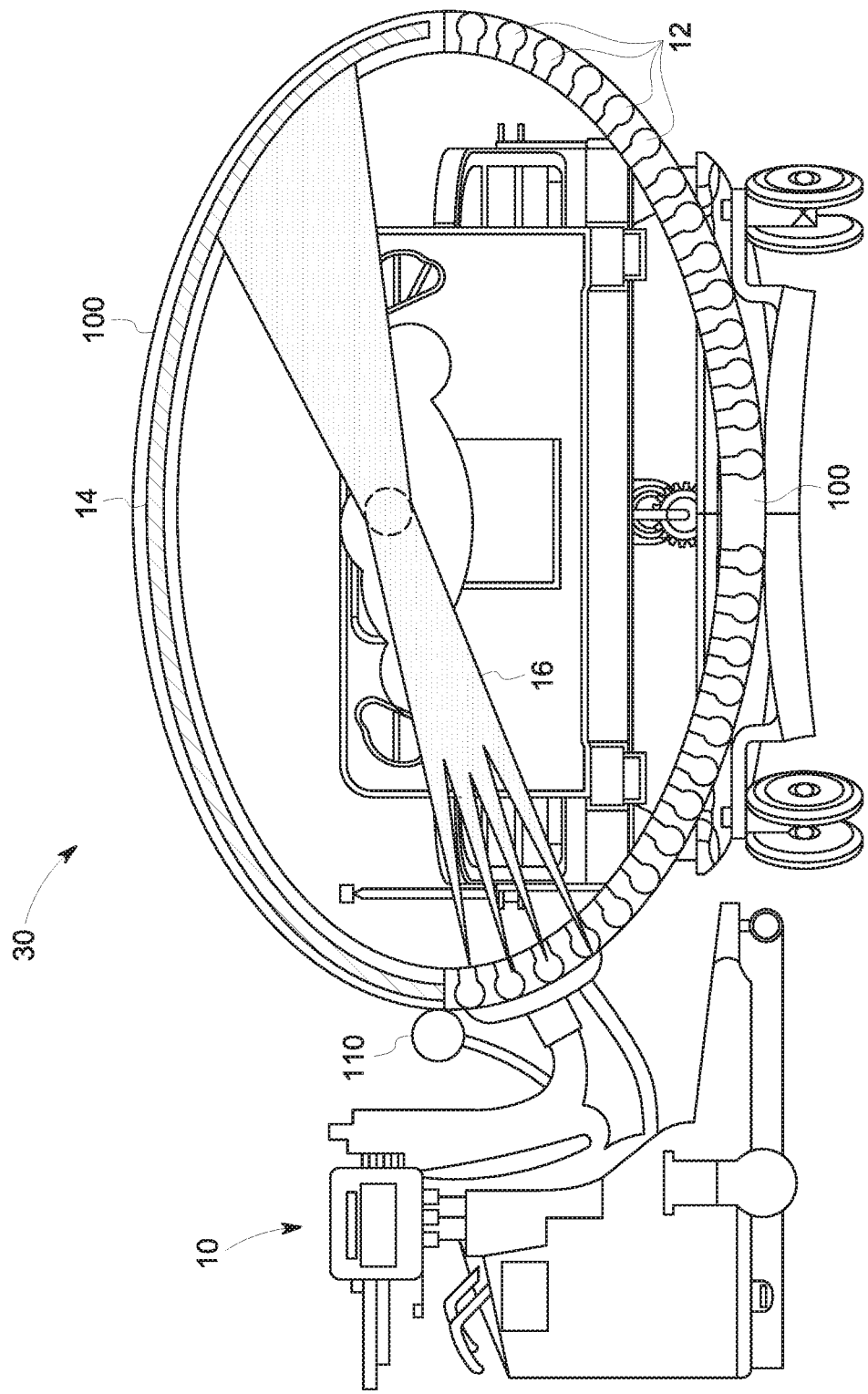
FIG. 11 depicts an implementation of an implementation of a C-shaped imager illustrating a curved array of X-ray sources and a curved detector array, in accordance with aspects of the present disclosure.

While the preceding examples depict structural configurations of certain embodiments, FIG. 11 depicts one example (here a hinged example) in which imaging components are shown by way of a cut-away view of the arms 100. In this example, the lower arm is cut away to reveal a plurality of X-ray tubes 12 each configured to emit X-rays 16 toward and through an imaging volume from a different angular position. By way of example, such X-ray sources 12 may be operated in a sequential manner so that only one source (or a limited subset of sources) is active at a time or may be operated so that multiple sources 12 are active at one time but are activated in subsets such that overlapping of emitted X-rays on the detector(s) 14 from different X-ray sources 12 does not occur.

In this and the preceding examples the X-ray sources 12 may be provided as an array of discrete X-ray tubes (in which each tube has its own vacuum chamber) or the array of X-ray sources 12 may be implemented as a distributed source with an array of focal spots (which in this context may referred to as sources or source spots) within a shared or common vacuum chamber. In certain embodiments, the array of X-ray sources 12 extends over a substantial portion of the arm 100 (e.g. >20 degrees) such that X-rays 16 are emitted from substantially different angles towards the patient, giving some level of intrinsic tomographic capability, even without mechanical movement.

With reference back to the implementations shown in FIGS. 6-10, and with the components shown in the example of FIG. 11 in mind, the X-ray sources 12 can be activated simultaneously, sequentially, or in grouped sequences (e.g., X-ray tubes 1, 11, and 21 activated then deactivated, followed, by X-ray tubes 2, 12, and 22, and so forth). Further, depending on the imaging protocol, the X-ray sources 12 can be operated using a single tube voltage or multiple tube voltages and/or a single tube current or multiple tube currents, to provide multi-spectral data for multi-spectral reconstruction and to optimize the radiation dose profile. Similarly, the different X-ray sources 12 may utilize the same filtration or different filtrations. In certain embodiments, such as the example shown in FIG. 11, given the spatial extent of the array of X-ray sources 12, tomographic data can be obtained without any mechanical movement of the arms 100 of the C-shaped imager. Alternatively, and as shown in the examples of FIGS. 6-10, the X-ray source(s) and/or detector array 14 may be moved (i.e., rotated) while active to acquire additional data from different positions to further enhance tomographic information.

The detector array 14 can, in certain implementations, consist of multiple, separate detector structures. For example, the detector array 14 may be formed using two or more flat-panel X-ray detectors fitted together so as to form a detector array 14 having the desired angular and/or longitudinal extent. Alternatively, the detector array 14 may be formed as a single, unitary extended detector (e.g., a curved or piecewise linear extended detector). Regardless of construction, the detector array 14 provides a detection surface on which X-rays transmitted through the patient during operation are incident and on which responsive electrical signals are generated for use in image reconstruction. In designs where the angular extent of the source or detector is still of limited size, the arcuate shape may revert to a linear shape, since a line segment can be interpreted as a small part of an arc.

With respect to various embodiments discussed herein, one aspect of the present embodiments is the ability to provide an imaging system capable of generating real-time 3D image data using a system being capable of use adjacent to a surgical table or other patient support. With that in mind, the system described herein may be mobile (i.e., capable of being moved to and from a patient bed or table) and may have a small footprint to allow medical personnel to remain with a patient and perform procedures on the patient even when the imaging system is present. Alternatively, in other implementations the C-shaped imager can attach to a side rail or other feature of the surgery table to improve alignment.

With the preceding structural and scanning examples in mind, the C-shaped imager systems described herein may be configured to operate in various scan and image reconstruction modes. By way of example, the C-shaped imager system may be configured to provide 2D projection X-ray images, such as lateral shots and anterior-posterior (AP) shots. Surgical instrumentation (e.g., tools), implants (e.g., hardware), and/or patient anatomical structures (such as vertebra) or organs may be tracked by using the imaging information acquired in such a manner. For example, the stereoscopic information of the lateral and AP images may be sufficient to determine the 3D position of rigid objects (such as implant screws, drills, needles, vertebra, bones, rigid organs, and so forth) involved in a surgical or therapy procedure.

In other implementations, acquired projection data over a suitable angular range may undergo tomographic reconstruction, such as using iterative reconstruction, filtered backprojection, backprojection, compressed sensing, or deep learning techniques. Pre-operative images, such as from a standard computed tomography (CT), ultrasound (U/S) or magnetic resonance imaging (MM) scanner, can be used as prior information during the reconstruction of the intra-operative imager data acquired using the C-shaped imager. Specifically, using this prior information, certain of these tomographic reconstruction techniques may enable the use of sparse, limited-angle and low-dose C-shaped imager data to generate useful tomographic reconstructions. For instance, 2 to 100 projections may be reconstructed to generate a useful tomographic reconstruction using such prior information, in comparison to the acquisition and use of up to 1000 projections for a standard CT reconstruction. Correspondingly, the dose levels of a single C-shaped imager scan using a system and scanning methodology as described herein may be on the order of 0.1 mSv, in comparison to 2 mSv for a standard CT scan.

Technical aspects of the invention include a C-shaped imager system having an arcuate array of X-ray sources and an arcuate detector array. The C-shaped imager system, in certain embodiments, has an open configuration and a closed configuration as well as a reduced footprint such that the imaging system can be used in surgical and interventional contexts to provide real-time 3D images, thereby providing feedback in real-time during a procedure so as to reduce returning to a surgical procedure in response to post-operative imaging.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
   a support structure comprising:
      a first arm comprising an array of X-ray emission points;
      a second arm comprising a detector array;
      wherein the first arm and the second arm are movable between an open configuration and a closed configuration;
   a system controller in communication with the array of X-ray emission points and the detector array;
   a display device configured to display images generated using data acquired using the detector array;
   wherein the system controller is configured to generate the images displayed on the display device in real-time and wherein the images include three-dimensional images comprising approximately isotropic voxels or oblique reformats thereof;
   wherein the system controller is configured to generate the images using data acquired from the detector array and using pre-operative imaging data as prior information;
   wherein the each of the X-ray emission points simultaneously emit X-rays toward a separate detector of the detector array.

2. The X-ray imaging system of claim 1, wherein the array of X-ray emission points comprises an arcuate array of X-ray emission points and wherein the detector array comprises an arcuate detector array.

3. The X-ray imaging system of claim 1, wherein the first arm and the second arm are connected by a hinge to allow movement of the first arm and the second arm between the open configuration and the closed configuration.

4. The X-ray imaging system of claim 1, wherein one or both of the first arm and the second arm comprise slidable arcuate structures which slide to move the first arm and the second arm between the open configuration and the closed configuration.

5. The X-ray imaging system of claim 1, wherein the array of X-ray emission points and the detector array provide at least 90 degrees of angular coverage with respect to an imaged volume when the first arm and the second arm are in the closed configuration.

6. The X-ray imaging system of claim 1, wherein the array of X-ray emission points comprise a plurality of X-ray tubes, wherein each X-ray tube corresponds to a respective X-ray emission point.

7. The X-ray imaging system of claim 1, wherein the system controller is configured to cause simultaneous emission of X-rays from each X-ray emission point during operation.

8. The X-ray imaging system of claim 1, wherein at least one X-ray emission point is mechanically rotated about an imaged volume during operation.

9. The X-ray imaging system of claim 1, wherein the first arm and the second arm, when in the open configuration, are positionable about a patient on a bed or on an operating table and, when in the closed configuration are positioned to image the patient.

10. The X-ray imaging system of claim 1, wherein the pre-operative imaging data comprises pre-operative data obtained historically from other imaging modalities and wherein the other imaging modalities include at least one of a computed tomography (CT), magnetic resonance imaging (MM) or ultrasound (U/S).

11. A method for imaging a patient, comprising:
positioning a C-shaped imager proximate to a patient, wherein the C-shaped imager comprises a first arm and a second arm in an open configuration such that the first arm and the second arm go about the patient in the open configuration, wherein the first arm comprises an array of X-ray emission points and the second arm comprises a detector array;
causing the first arm and the second arm to move to a closed configuration about the patient, wherein the closed configuration is suitable for imaging the patient;
operating the C-shaped imager to acquire X-ray projection data over an angular range about the patient;
generating one or more images using the acquired X-ray projection data;
displaying in real-time the one or more images;
wherein the one or more images are three-dimensional images comprising approximately isotropic voxels or oblique reformats thereof;
wherein the one or more images are generated using data acquired using the X-ray projection data and using pre-operative imaging data as prior information;
wherein the each of the X-ray emission points simultaneously emit X-rays toward a separate detector of the detector array.

12. The method of claim 11, wherein the first arm and second arm are connected by a hinge and wherein causing the first arm and the second arm to move to the closed configuration comprises causing the first arm and the second arm to swing toward one another.

13. The method of claim 11, wherein one or both of the first arm and the second arm comprise slidable arcuate structures and wherein causing the first arm and the second arm to move to the closed configuration comprises causing the slidable arcuate structure to slide relative to one another.

14. The method of claim 11, wherein the array of X-ray emission points and the detector array provide at least 90 degrees of angular coverage with respect to the patient when the first arm and the second arm are in the closed configuration.

15. The method of claim 11, wherein operating the C-shaped imager to acquire X-ray projection data over an angular range about the patient comprises simultaneously emitting X-rays from each X-ray emission point during operation.

16. The method of claim 11, further comprising:
accessing pre-operative imaging data;
wherein generating the one or more images comprises using the data acquired using the detector array and using the pre-operative imaging data as prior information.

17. An X-ray imaging system, comprising:
a C-shaped imager comprising:
  a first arm comprising an array of multiple X-ray emission points;
  a second arm comprising a detector array configured to detect X-rays emitted by the array of multiple X-ray emission points, wherein the array of multiple X-ray emission points and the detector array provide at least 90 degrees of angular coverage with respect to an imaged volume when the first arm and the second arm are in a closed configuration;
a system controller in communication with the array of X-ray emission points and the detector array;
a display device configured to display images generated using data acquired using the detector array;
wherein the system controller is configured to generate the images displayed on the display device in real-time and wherein the images include three-dimensional images comprising approximately isotropic voxels or oblique reformats thereof;
wherein the system controller is configured to generate the images using data acquired from the detector array and using pre-operative imaging data as prior information; and
wherein the each of the X-ray emission points simultaneously emit X-rays toward a separate detector of the detector array.

18. The X-ray imaging system of claim 17, wherein the first arm can be mechanically rotated to extend the angular coverage of the X-ray emission points with respect to the patient.

19. The X-ray imaging system of claim 17, wherein the system controller is configured to cause simultaneous emission of X-rays from each X-ray emission point during operation.

* * * * *